(12) United States Patent
Ducharme

(10) Patent No.: US 8,066,715 B2
(45) Date of Patent: Nov. 29, 2011

(54) MAGNETIC STENT REMOVAL

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 604 days.

(21) Appl. No.: 11/866,824

(22) Filed: Oct. 3, 2007

(65) Prior Publication Data

US 2009/0093822 A1    Apr. 9, 2009

(51) Int. Cl.
  *A61F 11/00* (2006.01)
  *A61F 2/04* (2006.01)
  *A61M 5/00* (2006.01)

(52) U.S. Cl. .......... 606/108; 623/23.64; 623/23.7; 604/8

(58) Field of Classification Search ........ 623/1.11, 623/1.12, 1.23, 23.64–23.7; 604/540–544; 606/108, 191–193; 600/12; 128/899
See application file for complete search history.

(56) References Cited

U.S. PATENT DOCUMENTS

| | | | | |
|---|---|---|---|---|
| 3,005,458 A | * | 10/1961 | Brook et al. | 606/106 |
| 3,358,676 A | * | 12/1967 | Frei et al. | 600/12 |
| 3,683,890 A | * | 8/1972 | Beal | 600/371 |
| 3,908,646 A | | 9/1975 | Ansari | |
| 4,315,509 A | * | 2/1982 | Smit | 606/108 |
| 4,657,020 A | * | 4/1987 | Lifton | 606/106 |
| 4,790,809 A | | 12/1988 | Kuntz | |
| 4,865,030 A | | 9/1989 | Polyak | |
| 4,925,446 A | * | 5/1990 | Garay et al. | 604/103.02 |
| 4,957,479 A | | 9/1990 | Roemer | |
| 4,989,299 A | | 2/1991 | Morita | |
| 4,992,768 A | * | 2/1991 | Mozis et al. | 335/306 |
| 5,096,763 A | * | 3/1992 | Ogata et al. | 428/76 |
| 5,176,626 A | | 1/1993 | Soehendra | |
| 5,334,208 A | | 8/1994 | Soehendra et al. | |
| 5,353,807 A | * | 10/1994 | DeMarco | 600/585 |
| 5,466,242 A | * | 11/1995 | Mori | 606/198 |
| 5,514,176 A | | 5/1996 | Bosley, Jr. | |
| 5,643,277 A | | 7/1997 | Soehendra et al. | |
| 5,647,843 A | | 7/1997 | Mesrobian et al. | |
| 5,663,701 A | * | 9/1997 | Kaura | 335/306 |

(Continued)

FOREIGN PATENT DOCUMENTS

EP      1 600 121 A1    11/2005

(Continued)

OTHER PUBLICATIONS

Wikipedia, the Free Encyclopedia. "Small Intestine". Downloaded from <http://en.wikipedia.org/wiki/Small_intestine> on Jan. 28, 2010.*

(Continued)

*Primary Examiner* — David Isabella
*Assistant Examiner* — Andrew Iwamaye
(74) *Attorney, Agent, or Firm* — Brinks Hofer Gilson & Lione

(57) ABSTRACT

A medical device and method for its use in the digestive system of a mammalian patient is provided. The medical device includes a stent and a retrieval device. The stent has a magnetic element connected to an end of the stent. The retrieval device includes a magnetic member, and the retrieval device is sized to be ingested by the patient. The magnetic member is capable of being magnetically coupled to the magnetic element of the stent for removal of the stent through the natural forces of the digestive system.

8 Claims, 5 Drawing Sheets

U.S. PATENT DOCUMENTS

| | | | |
|---|---|---|---|
| RE35,849 E | 7/1998 | Soehendra | |
| 5,800,517 A | 9/1998 | Andersone et al. | |
| 5,876,450 A | 3/1999 | Johlin, Jr. | |
| 6,202,596 B1* | 3/2001 | Lopez et al. | 119/174 |
| 6,258,098 B1 | 7/2001 | Taylor et al. | |
| 6,652,569 B1 | 11/2003 | Taylor et al. | |
| 6,676,694 B1* | 1/2004 | Weiss | 623/1.11 |
| 7,011,094 B2* | 3/2006 | Rapacki et al. | 128/207.15 |
| 7,850,708 B2 | 12/2010 | Pal | 606/200 |
| 7,892,292 B2* | 2/2011 | Stack et al. | 623/23.65 |
| 2003/0060894 A1* | 3/2003 | Dua et al. | 623/23.68 |
| 2003/0216622 A1* | 11/2003 | Meron et al. | 600/300 |
| 2004/0127787 A1* | 7/2004 | Dimmer et al. | 600/424 |
| 2004/0176797 A1* | 9/2004 | Opolski | 606/213 |
| 2005/0288555 A1* | 12/2005 | Binmoeller | 600/160 |
| 2007/0016131 A1 | 1/2007 | Munger et al. | |
| 2007/0270943 A1* | 11/2007 | Solem et al. | 623/2.11 |
| 2008/0035160 A1* | 2/2008 | Woodson et al. | 128/860 |
| 2008/0071383 A1* | 3/2008 | Levine et al. | 623/23.65 |
| 2008/0195226 A1* | 8/2008 | Williams et al. | 623/23.67 |
| 2008/0208265 A1* | 8/2008 | Frazier et al. | 606/326 |
| 2008/0236500 A1* | 10/2008 | Hodges et al. | 119/14.02 |
| 2010/0036241 A1* | 2/2010 | Mayse et al. | 600/435 |
| 2010/0137686 A1* | 6/2010 | Meron et al. | 600/118 |
| 2010/0145143 A1* | 6/2010 | Salomon et al. | 600/104 |

FOREIGN PATENT DOCUMENTS

| | | |
|---|---|---|
| WO | WO 03/103541 A1 | 12/2003 |
| WO | WO 2007/035798 A2 * | 3/2007 |

OTHER PUBLICATIONS

Brochure entitled "Tiger Tube" Self-advancing Nasal Jejunal Feeding Tube—COOK Interventional Critical Care Products.

Wiley Encyclopedia of Biomedical Engineering, entitled "STENTS" (10 pages) by C. Lally et al. Copyright 2006 John Wiley & Sons, Inc.

International Search Report and Written Opinion (PCT/US08/73081) dated Oct. 27, 2008 in related application.

* cited by examiner

MAGNETIC STENT REMOVAL

FIELD OF THE INVENTION

The present invention relates generally to stents used in body lumens of the gastrointestinal system such as pancreatic and biliary stents, and more particularly relates to devices and methods for retrieval of such stents.

BACKGROUND OF THE INVENTION

Stents used within the gastrointestinal system, such as biliary stents or pancreatic stents, are generally tubular plastic structures, although metal stents and expandable stents are also sometimes employed. Delivery of these stents is usually accomplished in an endoscopic procedure (e.g. see U.S. Pat. No. 5,876,450). Likewise, retrieval of such stents is accomplished in a separate endoscopic procedure. Retrieval may be accomplished using specialized retrieval devices such as those disclosed in U.S. Pat. Nos. 5,334,208 and 5,643,277, or more conventional devices such as grasping forceps or snares. Some degree of direct visualization of both the stent and device are required in order to retrieve the stents, thus giving rise to the need for the separate endoscopic procedure for removal.

Unfortunately, these stents can sometimes migrate up a patients duct, rendering them difficult to remove. As endoscopic stenting procedures in the biliary and pancreatic ducts become more prevalent, the medical challenge in retrieving these stents will increase. Accordingly, there exists a need to provide devices and methods for retrieval of gastrointestinal stents which improve the ability to remove the stent, including once the stent has migrated up a patient's duct or which otherwise does not require direct visualization of the stent and retrieval device.

BRIEF SUMMARY OF THE INVENTION

The present invention provides a medical device and related methods for retrieving a stent which aids in retrieval even when the stent has migrated from its initial placement, and further does not require direct visualization of the retrieval device or stent. As such, the medical device and methods do not require a second endoscopic procedure, thereby reducing costs, procedure time and expense. According to one embodiment of the present invention, a medical device for use in the digestive system of a mammalian patient is provided and generally comprises a stent and a retrieval device. The stent has a magnetic element connected to an end of the stent. The retrieval device includes a magnetic member, and is sized to be swallowed in its entirety by the patient. The magnetic member is capable of being magnetically coupled to the magnetic element of the stent for removal of the stent through the natural forces of the digestive system.

According to more detailed aspects of this embodiment, the magnetic element may be directly connected to the end of the stent, or may be indirectly connected to the end of the stent via a tether. The stent is preferably placed within a body lumen of the digestive system, such as the pancreatic or biliary duct, and the retrieval device is structured to be forced downstream by peristaltic contractions of the duodenum.

The retrieval device and its magnetic member preferably have a force of attraction to the magnetic element that is greater than the force imposed upon the magnetic member by the peristaltic contractions of the duodenum. Likewise, the force of attraction is preferably greater than the friction between the stent and the pancreatic or biliary duct.

According to still further aspects, the retrieval device preferably includes a tail connected to the magnetic member. The tail is constructed of a flexible material and is sized to be swallowed by the patient together with the magnetic member. The tail is elongated and has a length greater than the length of the magnetic member. In one version, the tail is tubular and may have a diameter that is constant or increases or decreases along its length. In another version, the tail is formed by a plurality of strips. In yet another version, the tail is a sheet connected to the magnetic member by one or more tethers. Preferably the sheet and tethers are structured to form a parachute. The magnetic member may also include a protective coating. The protective coating may be made of a digestive-resistant material, including both plastics and metals. The magnetic member or its protective coating may have a roughened area to improve ultrasound imaging of the retrieval device.

According to another embodiment in accordance with the teachings of the present invention, a method for retrieving a stent placed within a body lumen of the digestive system is provided. The stent includes a magnetic element connected to an end of the stent. A magnetic member is provided having a size suitable for being ingested by the patient, and is capable of being magnetically coupled to the magnetic element of the stent. The magnetic member is ingested, and time is allowed for the magnetic member to pass naturally through the digestive tract and become magnetically coupled to the magnetic element of the stent. The natural action of the digestive system acts on the magnetic member to remove the stent from the body lumen.

According to more detailed aspects of the invention, the method may further include the steps of providing a plurality of magnetic members each having a size suitable for being swallowed by the patient and capable of being magnetically coupled to the magnetic element of the stent. The plurality of magnetic members may such include a different structure. The plurality of magnetic members may be provided and swallowed, separately or together.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
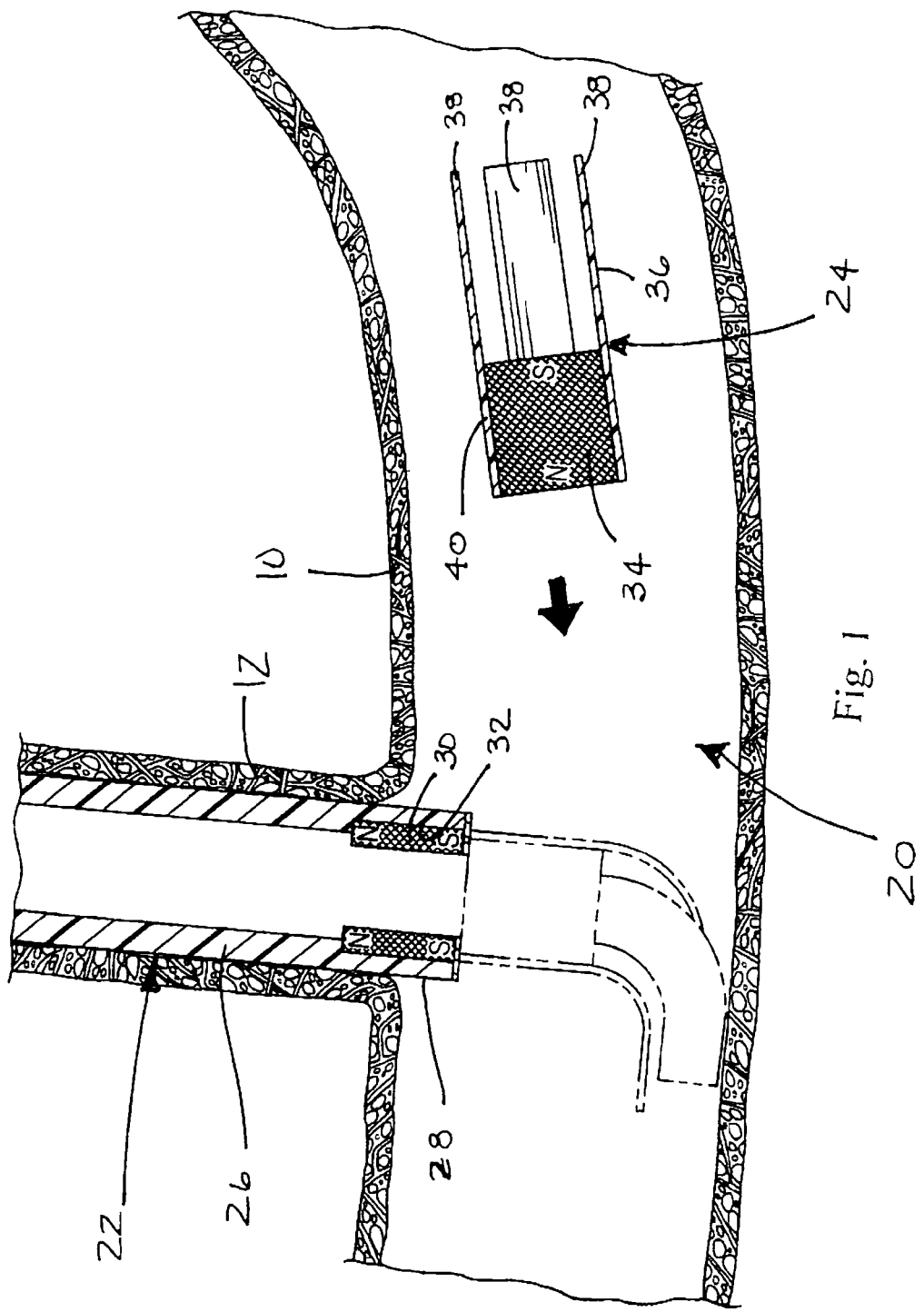
FIG. 1 is a cross-section view of a medical system including a stent and retrieval device, constructed in accordance with the teachings of the present invention.

Turning now to the figures, FIG. 1 depicts a medical system 20 for use in the digestive system of a mammalian patient, constructed in accordance with the teachings of the present invention. The medical system 20 generally comprises a stent 22 and a retrieval device 24. The stent 22 is of the type designed for use in the digestive system, such as a biliary stent or pancreatic stent. As noted in the background section, such stents are typically polymeric tubes for providing a conduit, although metal stents, both expanding and non-expanding, and generally all known or future developed stents may be adapted for use as part of the medical device of the present invention. As depicted, the stent 22 includes a polymeric tube 26 having a proximal end 28. The stent 22 has been positioned within the biliary duct 12 such that the proximal end 28 projects slightly into the duodenum 10 of the small intestines. The proximal end 28 of the stent 22 defines a pocket 32 sized to receive and retain a magnetic element 30. The tube 26 and magnetic element 30 may be connected in numerous ways, including adhesives, bonding, mechanical retention structures, fasteners and the like (see, e.g. U.S. Pat. No. 4,790,809, the disclosure of which is incorporated herein by reference in its entirety).

Figure 2:
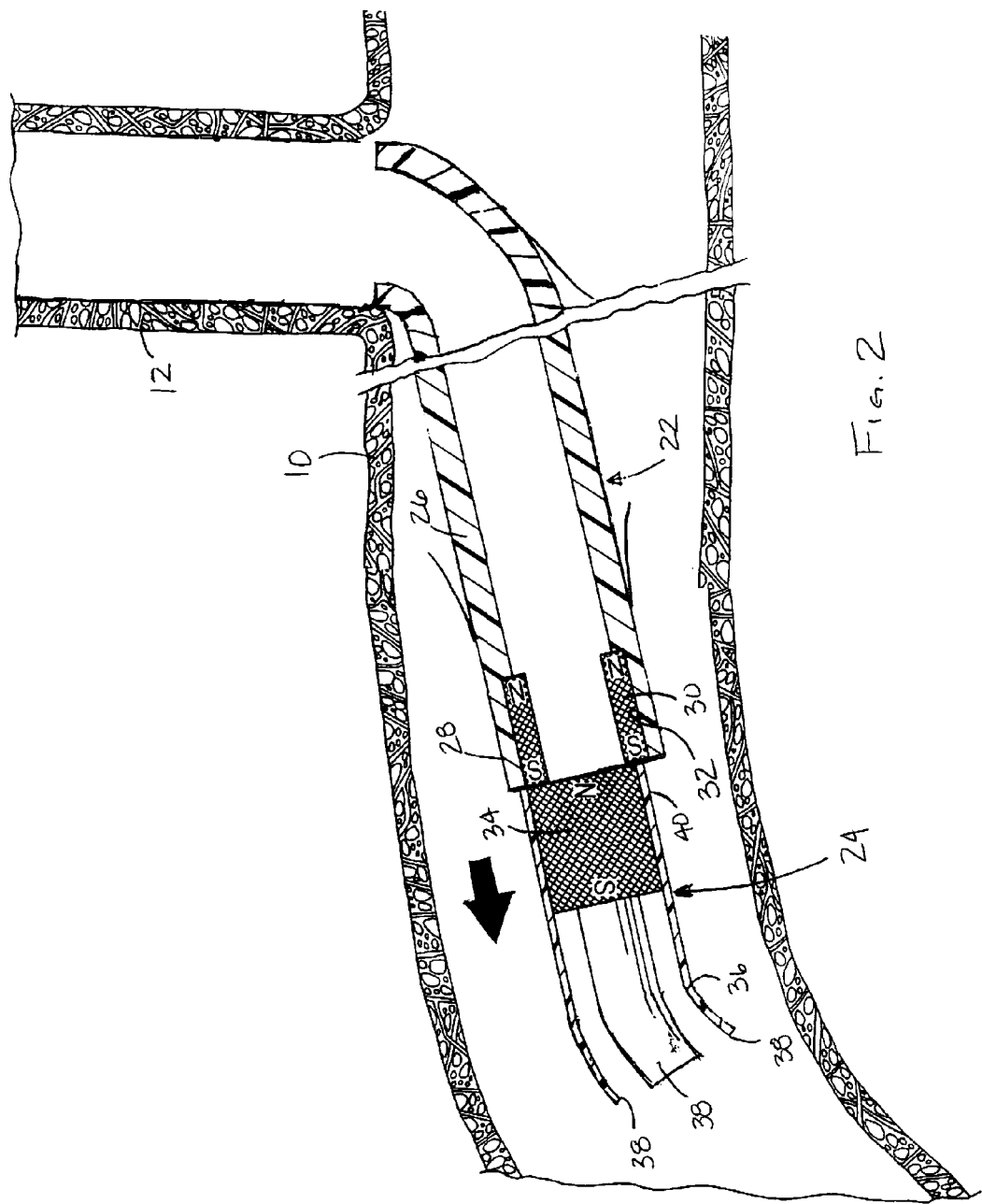
FIG. 2 is a cross-section view of a medical system including a stent and retrieval.
Figure 3:
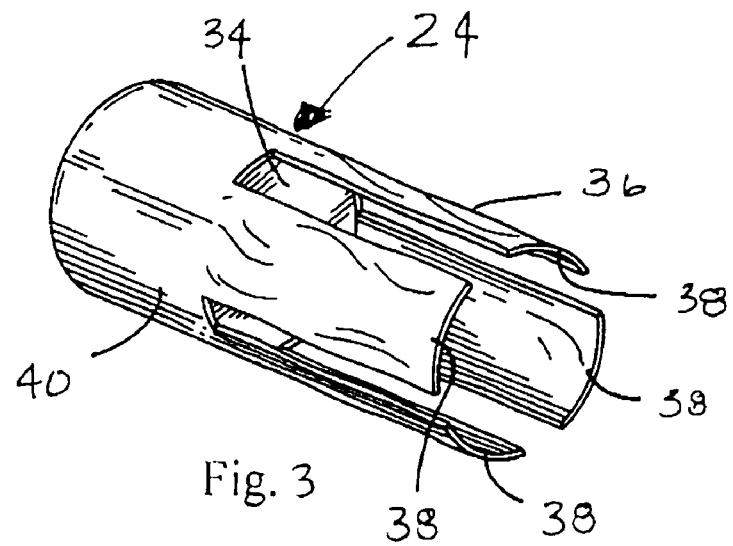
FIG. 3 is a perspective view of the retrieval device depicted in FIG. 1.

The retrieval device 24 generally comprises a magnetic member 34 and a tail 36. As shown in FIGS. 1-3, the tail 36 generally includes a plurality of polymeric strips 38 which are connected to the magnetic member 34 and project away therefrom. The strips 38 are connected to the outer surface of the cylindrical magnetic member 34, and are circumferentially spaced, although it will be recognized by those skilled in the art that the strips 38 may be attached to any portion of the magnetic member 34 and may overlap. The tail 36 (and its strips 38) is preferably longer (i.e. axial length) than the magnetic member 34. In the depicted embodiment, the magnetic member 34 has been provided with a protective polymeric coating 40 and the tail 36 has been integrally and unitarily formed with the protective coating 40. The plastics used for forming the protective coating 40 and/or the tail 36 are preferably formed of a digestive-resistant material, although this is not necessary. Many well-known plastics have suitable properties for forming these components, including selected parylene, polyesters, polyurethanes, polyethylenes, polyamides, and silicone to name a few. Likewise, the protective coating 40 and/or the tail 36 may be formed of various metals or alloys. As noted above regarding the stent, conventional techniques for connecting the magnetic member 34 and tail 36 may be employed.

As shown by the dotted lines in FIG. 1, the retrieval device 24 and its magnetic member 34 are designed to become magnetically coupled to the magnetic element 30 of the stent 22. As used herein, magnetic refers to all magnetically attractable materials, such as magnets and magnetically charged members, as well as ferrous materials such as iron, nickel, cobalt, steel and various alloys that are attractable to a magnet. By way of example, both the magnetic element 30 and magnetic member 34 have been depicted as magnets, although it will be recognized by those skilled in the art that only one of the magnetic components may be a magnet while the other is a ferrous material or other material that is simply attracted to the one magnet. Rare earth magnets are ideally employed. It can also be seen that the poles (depicted as north N and south S in the figures) of the magnetic element 30 and magnetic member 34 are oriented to promote the magnetic coupling of the stent 22 and retrieval device 24. As shown, the southern pole S of the magnetic element 30 has been depicted as proximally facing, while the attracted northern pole N of the magnetic member 34 has been positioned opposite the tail 36 for directly engaging the magnetic element 30.

In practice, the retrieval device 24 is sized to be ingested whole by the patient, such as by swallowing the device 24 or introducing it through the upper GI tract by the medical professional. Preferably sizes of the retrieval device include diameters in the range of 0.125 to 0.5 inches and the lengths of 0.25 to 3 inches, although retrieval devices 24 outside of these ranges may be suitable for being swallowed depending upon the size and type of mammalian patient. Although depicted as cylindrical for ease of swallowing, the retrieval device 24 and its magnetic member 34 may be designed to have numerous types of cross-sectional shapes such as oblong or oval, square, triangular, etc.

In accordance with the teachings of the present invention, the method for retrieving the stent 22 includes ingesting the retrieval device 24 and allowing it to pass through the digestive system to a position proximate the stent 22, depicted here as in the biliary duct 12 and adjacent the duodenum 10. The retrieval device 24 becomes magnetically coupled to the proximal end of the stent 22, as depicted by the dotted lines in FIG. 1. By design, the natural peristaltic action of the duodenum 10 will act upon the retrieval device 24, and in particular both the magnetic member 34 and tail 36. The tail 36 may take other forms than shown, such as extending laterally (inwardly or outwardly) and/or being curved to improve engagement with the gastrointestinal tract and improve response to peristaltic action. The natural action of the digestive system thus serves to overcome the friction between the stent 22 and biliary duct 12 and withdraw the stent 22, as shown in FIG. 2. Depending on location within the digestive system, other natural body functions and action can act on the retrieval device 24 for stent 22 removal, including contractions, spasms, the flow of fluids, pressure differentials and the like.

Accordingly, the force of magnetic attraction between the magnetic element 30 and magnetic member 34 is preferably designed to be greater than the forces imposed by the peristaltic action of the duodenum 10, as well as greater than the frictional force between the stent 22 and biliary duct 12 (or other body lumen of the digestive system in which the stent 22 is placed). Preferably, the force of magnetic attraction is in the range of 1 to 20 Newtons, and most preferably about 4N to about 10N. Likewise, the weight of the retrieval device 24 helps work the stent 22 out of the duct 12 and through the gastrointestinal tract due to gravitational action.

Once removed, the retrieval device 24 and stent 22 are allowed to naturally pass through the digestive system. In some situations, it may be desirable to simply use the retrieval device 24 to draw down a stent 22 that has migrated up the biliary duct 12 or other bodily lumen, and then employ a follow-up endoscopic procedure to retrieve the stent 22 and/or retrieval device 24.

Figure 4:
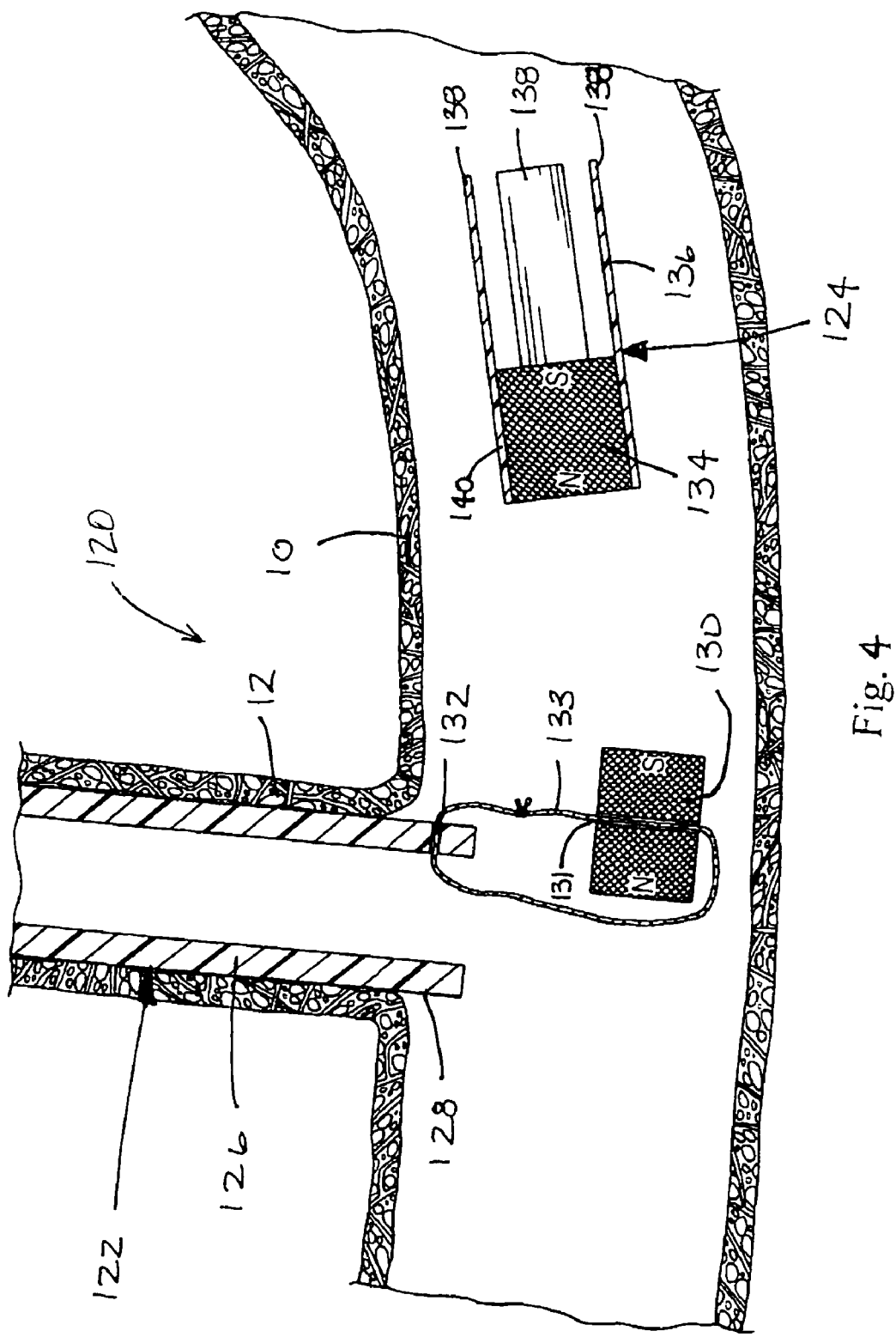
FIG. 4 is a cross-sectional view of another embodiment of the stent forming a portion of the medical device, constructed in accordance with the teachings of the present invention.

It will be recognized by those skilled in the art that many modifications to the medical system 20 will be readily contemplated by those skilled in the art. For example, FIG. 4 depicts an alternate embodiment of a medical system 120 comprising a stent 122 and retrieval device 124. The retrieval device 124 is substantially identical to the device depicted in FIG. 1, and generally includes a magnetic member 134 and a tail 136 comprised of a plurality of strands 138. The magnetic member 134 includes a coating 140 which is also used to form the strands 138 of the tail 136. In this embodiment, however, the stent 122 includes a differently structured magnetic element 130. The stent 122 is formed by a polymeric tube 126 having a proximal end which includes an aperture 132 formed therein. The magnetic element 130 is connected to the proximal end 128 by way of the aperture 132 therein and a tether 133. The tether may be formed with numerous types of materials, such as a suture, although any type of string or strap may be employed. The magnetic element 130 includes a passageway 131 for receiving the tether 133. By way of this embodiment, it will be recognized that even if the polymeric tube 126 of the stent 122 migrates up into the biliary duct 12 (or other body lumen) the magnetic element 130 will tend to remain proximate the duodenum 10 for easy retrieval using the retrieval device 124. As in the prior embodiment, the natural forces of the digestive system will act on the retrieval device 124 to pull on the stent 122 and withdraw it from the bodily lumen 12.

Figure 5:
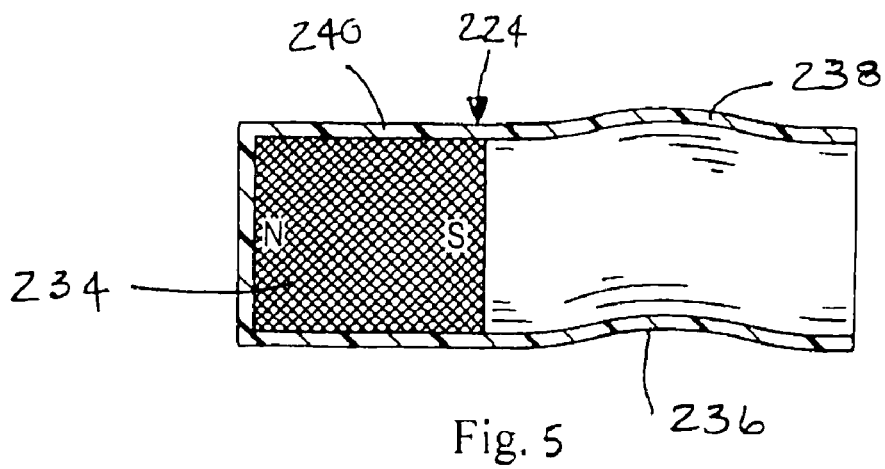
FIG. 5 is a cross-sectional view of an alternate embodiment of the retrieval device depicted in FIGS. 1-4, constructed in accordance with the teachings of the present invention.

It will also be recognized that numerous modifications to the retrieval device 124 are contemplated. Turning now to FIG. 5, an alternate retrieval device 224 generally includes a magnetic member 234 and a tail 236. In this embodiment, the tail 236 is formed as a flexible tube 238. The flexible tube 238 has a generally cylindrical configuration, although any tubular cross-sectional shape may be employed (square, oval, triangular, etc.) As in the prior embodiment, the protective coating 244 covers the magnetic member 234, and the coating 240 is entirely and unitarily formed with the tail 236. It will also be recognized that the protective coating 240 covers the nose of the magnetic member 234, and generally encapsulates the same.

Figure 6:
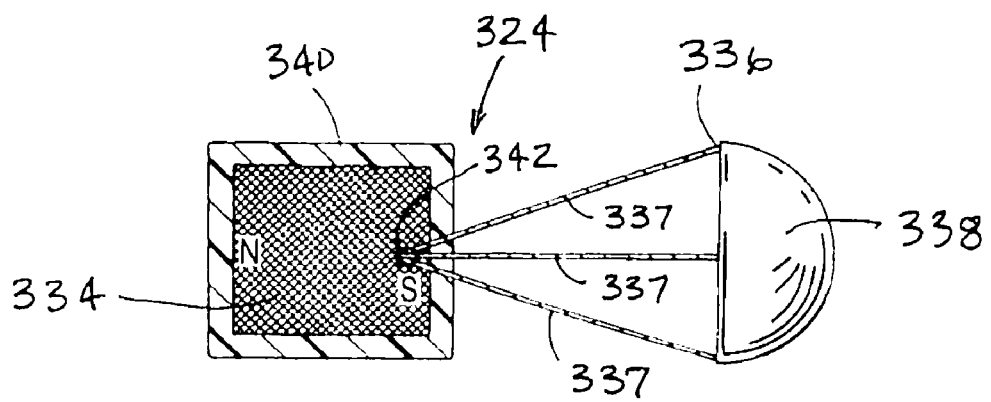
FIG. 6 is a partial cross-section of another embodiment of the retrieval device depicted in FIGS. 1-4, constructed in accordance with the teachings of the present invention.

As shown in FIG. 6, a retrieval device 324 again includes a magnetic member 334 and a tail 336. In this embodiment, the tail 336 generally comprises a parachute formed by a plurality of tethers 337 connected to a sheet of polymeric material 338. The magnetic member 334 has again been formed with an encapsulating protective coating 340. A passageway 342 has been formed in the magnetic member 334 for connecting the tethers 337 of the tail 336 to the magnetic member 334.

Figure 7:
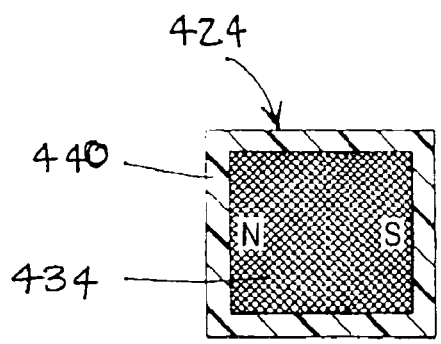
FIG. 7 is a cross-sectional view of an alternate embodiment of the retrieval device depicted in FIGS. 1-4, constructed in accordance with the teachings of the present invention.

In FIG. 7, the retrieval device 424 has been depicted simply as a magnetic member 434 having an encapsulating protective coating 440. Accordingly, it will be recognized that the tail portion of the various embodiments of the retrieval devices may be helpful in providing an additional structure and surface area on which the natural forces of the digestive system may act, but is not necessary to achieve the objects of the present invention.

Figure 8:
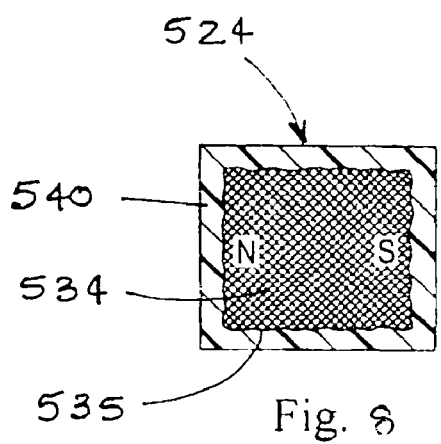
FIG. 8 is a cross-sectional view of an alternate embodiment of the retrieval device depicted in FIGS. 1-4, constructed in accordance with the teachings of the present invention.
Figure 9:
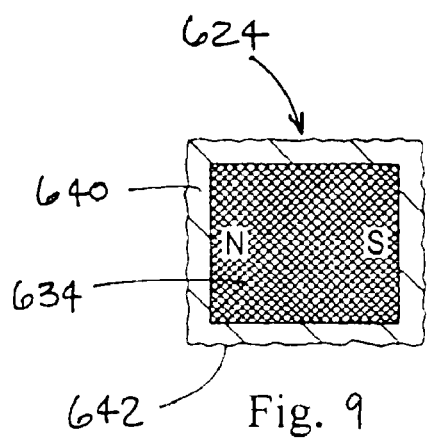
FIG. 9 is a cross-sectional view of an alternate embodiment of the retrieval device depicted in FIGS. 1-4, constructed in accordance with the teachings of the present invention.

FIGS. 8 and 9 show alternate embodiments of the retrieval device 424 depicted in FIG. 6, but also illustrate principles that may be applied to any of the embodiments of the retrieval device. In FIG. 8, the retrieval device 524 includes a magnetic member 534 and a protective coating 540. The exterior surface 535 of the magnetic member 534 has been roughened to improve ultrasonic imaging of the retrieval device 524. This will allow medical professionals to accurately determine when the retrieval device has been coupled to the stent in a non-invasive, yet reliable manner. In FIG. 9, the retrieval device 624 again includes a magnetic member 634 having a protective coating 640 formed thereon. However, in this embodiment, the protective outer layer 640 has been shown as formed of metal, and itself includes a roughened exterior surface 642. This construction of the exterior surface 642 of the outer layer 640 not only improves ultrasonic imaging capabilities, but also may be configured to increase the friction between the surface thereof and the interior walls of the bodily lumen to assist in permitting the natural forces of the digestive system to act on the retrieval device 624 and remove the stent from the particular body lumen.

Figure 10:
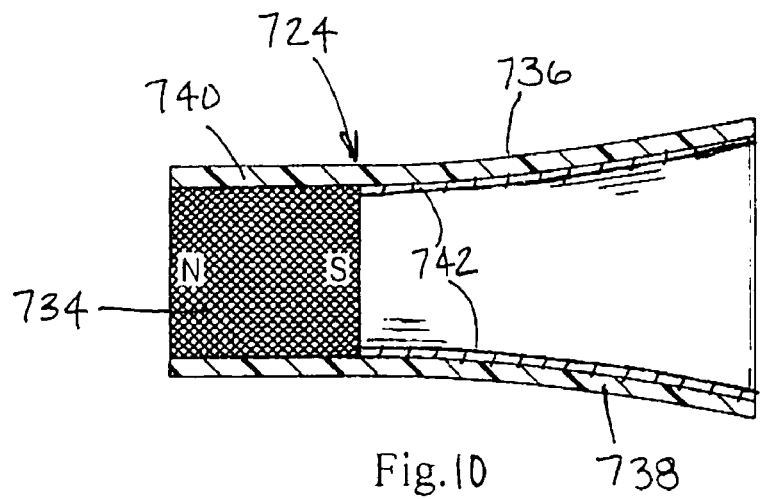
FIG. 10 is a cross-sectional view of an alternate embodiment of the retrieval device depicted in FIGS. 1-4, constructed in accordance with the teachings of the present invention.

Finally, in FIG. 10, still yet another embodiment of a retrieval device 724 has been depicted. The retrieval device 724 generally includes a magnetic member 734 and a tail 736. In this embodiment, the tail 736 has been shown as a flexible tube 738 which increases in diameter as it projects away from the magnetic member 734. Furthermore, a plurality of struts 742 are connected to the flexible tube 738 to maintain the structure thereof and prevent inversion over the magnetic member 734. The struts 742 may be formed of a resilient metal or plastic, and preferably are constructed of a shaped-memory alloy such as nitinol. Again, the magnetic member 734 includes a protective coating 740 which has been shown integrally formed with the flexible tube 738 of the tail 736.

With the numerous potential embodiments of the retrieval device, the method may further include the steps of providing a second magnetic member having a size suitable for being swallowed by the patient and capable of being magnetically coupled to the magnetic element of the stent. The second magnetic member is swallowed, and may include a structure different from the original magnetic member. Similarly, a third magnetic member may be provided and swallowed, which too can have a structure different from the first and second magnetic members. Using multiple retrieval devices, in succession, that have different structures may be desirable.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for use in a digestive system of a mammalian patient, the medical system comprising:
 a stent having a magnetic element connected to an end of the stent; and
 a retrieval device having a magnetic member and a tail, the tail including a sheet and a plurality of tethers connecting the sheet to the magnetic member to form a parachute, the retrieval device detached from the stent and sized to be ingested in its entirety by the mammalian patient;
 at least one of the magnetic element and magnetic member having a magnet, the magnetic member capable of being magnetically coupled to the magnetic element of the stent for removal of the stent from the mammalian patient;
 wherein coupling of the magnetic element and the magnetic member permits removal of the stent from a body lumen of the digestive system of the mammalian patient through natural forces of the digestive system acting on the retrieval device when the stent is disposed within the body lumen.

2. The medical system of claim 1, wherein the tail is constructed of a flexible material, the magnetic member and tail sized to be swallowed together by the mammalian patient.

3. The medical system of claim 1, wherein the plurality of tethers are connected to edges of the sheet to form the parachute.

4. The medical system of claim 1, wherein the magnetic member is a magnet.

5. The medical system of claim 1, wherein the magnetic member is non-expandable.

6. The medical system of claim 1, wherein the magnetic member is configured to be advanced downstream by peristaltic contractions of a duodenum when the stent is disposed within a pancreatic or biliary duct of the mammalian patient.

7. The medical system of claim 6, wherein a force of attraction between the magnetic element and magnetic member is greater than a force imposed on the magnetic member by the peristaltic contractions of the duodenum.

8. The medical system of claim 7, wherein the force of attraction between the magnetic element and magnetic member is greater than a frictional force between the stent and the pancreatic or biliary duct.

* * * * *